United States Patent [19]

Blackburn et al.

[11] Patent Number: 4,891,322
[45] Date of Patent: Jan. 2, 1990

[54] ASSAYING OF POLYNUCLEAR AROMATIC COMPOUNDS

[75] Inventors: Gary R. Blackburn, Washington Crossing, Pa.; Carl R. Mackerer, Pennington, N.J.; Ceinwen A. Schreiner, Meadowbrook, Pa.

[73] Assignee: Mobil Oil Corporation, New York, N.Y.

[21] Appl. No.: 18,111

[22] Filed: Feb. 24, 1987

[51] Int. Cl.$^4$ .................... G01N 33/00; G01N 21/00
[52] U.S. Cl. ........................................ 436/64; 436/29; 436/60; 436/110; 436/140; 436/164; 436/813
[58] Field of Search .................... 436/29, 60, 110, 140, 436/164, 64, 813

[56] References Cited

PUBLICATIONS

Litten et al., Relationship Between Fluorescence of Polynuclear Aromatic Hydrocarbons in Complex Environmental Mixtures and Sample Mutagenicity, 1982, 28(2) 141-8.
Wehry et al., Recent Developments in Matrix Isolation Spectroscopic Analysis of Polynuclear Aromatic Hydrocarbons, 1979, 1005-23.
Robinson et al., Handbook of Spectroscopy vol. II, 1980, pp. 134-214.
Campbell et al., "Nitrated Polycyclic Aromatic . . . " Carcinogenesis, vol. 2, No. 6, 559-565.
DiPaola et al., "Nitration of Carcinogenic . . . " Carcinogenesis, vol. 4, No. 3, pp. 357-359.
Rosenkrantz et al., "Mutagenicity . . . " Mutation Research, 114 (1983), pp. 217-219.
Towkiwa et al., "1-6-Dinitropyrene: Mutagenicity . . . " JNCI, vol. 73, No. 6, Dec. 1984, pp. 1359-1363.

*Primary Examiner*—Barry S. Richman
*Assistant Examiner*—Lyle Alfandary Alexander
*Attorney, Agent, or Firm*—Alexander J. McKillop; Charles J. Speciale

[57] ABSTRACT

A very rapid, sensitive method if provided for determination of the potential mutagenicity and/or carcinogenicity of certain petroleum oils by nitration of the oil and comparison of the light absorbance of its nitrated material with that obtained from one or more oils of known mutagenicity and/or carcinogenicity.

2 Claims, 3 Drawing Sheets

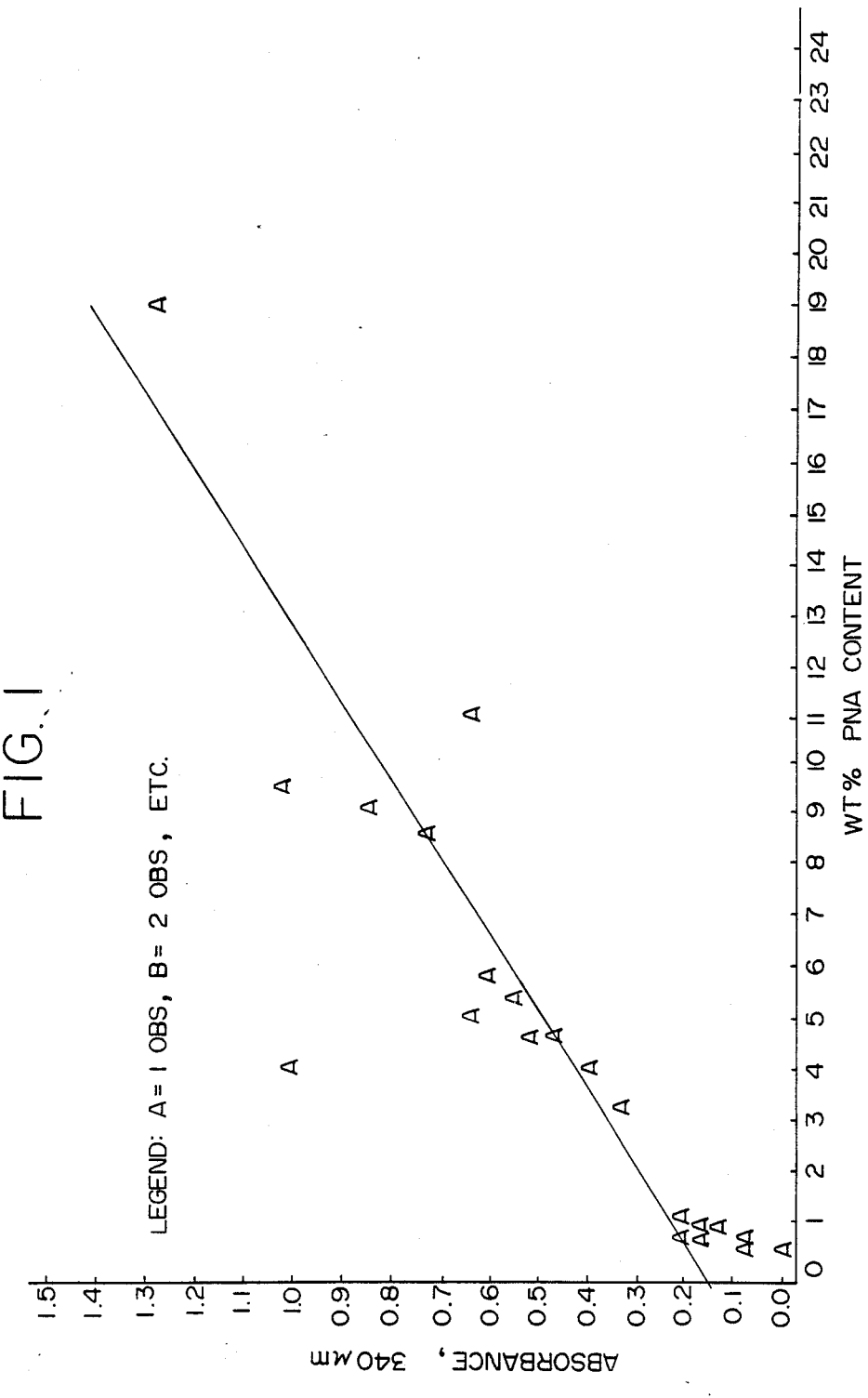

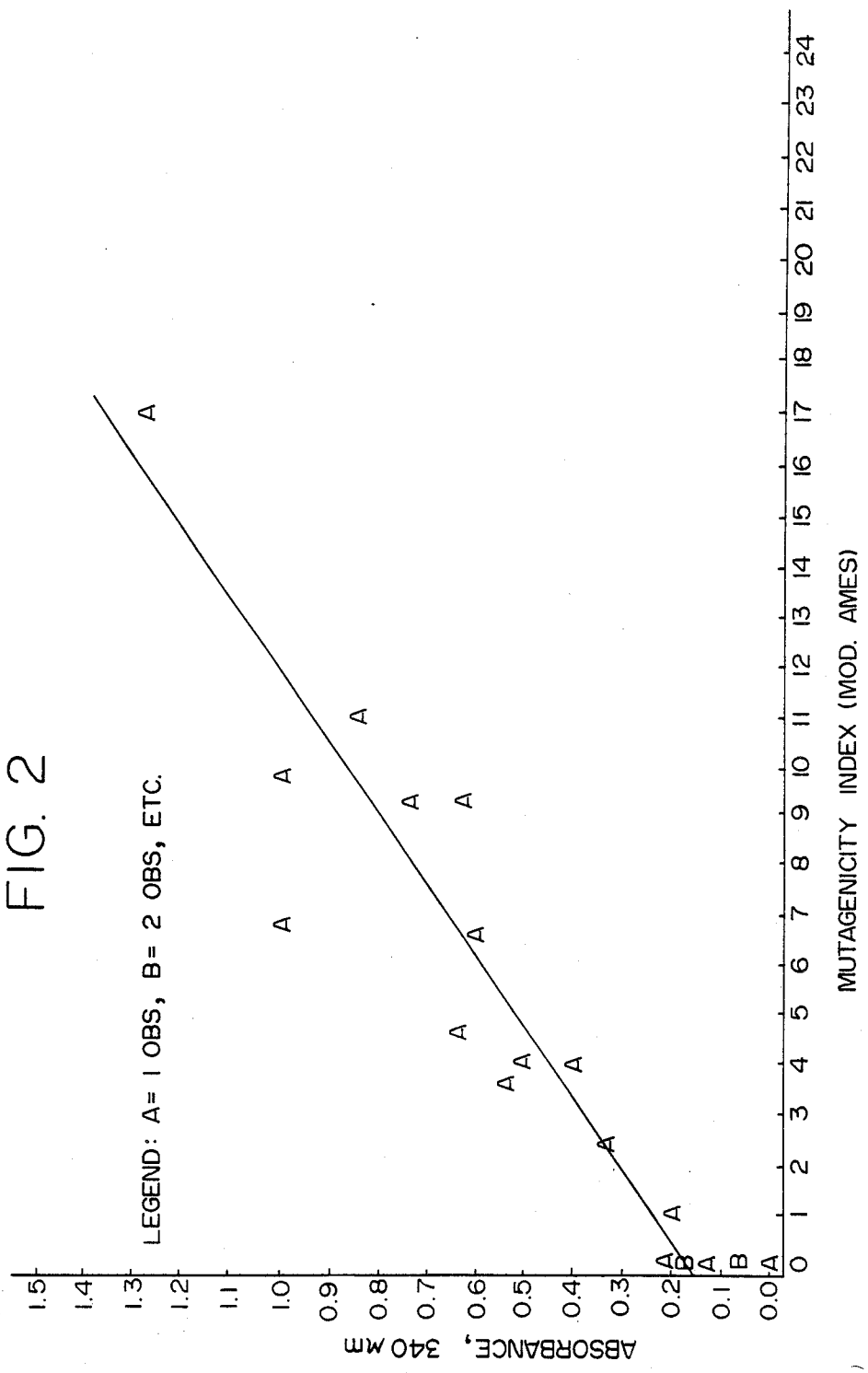

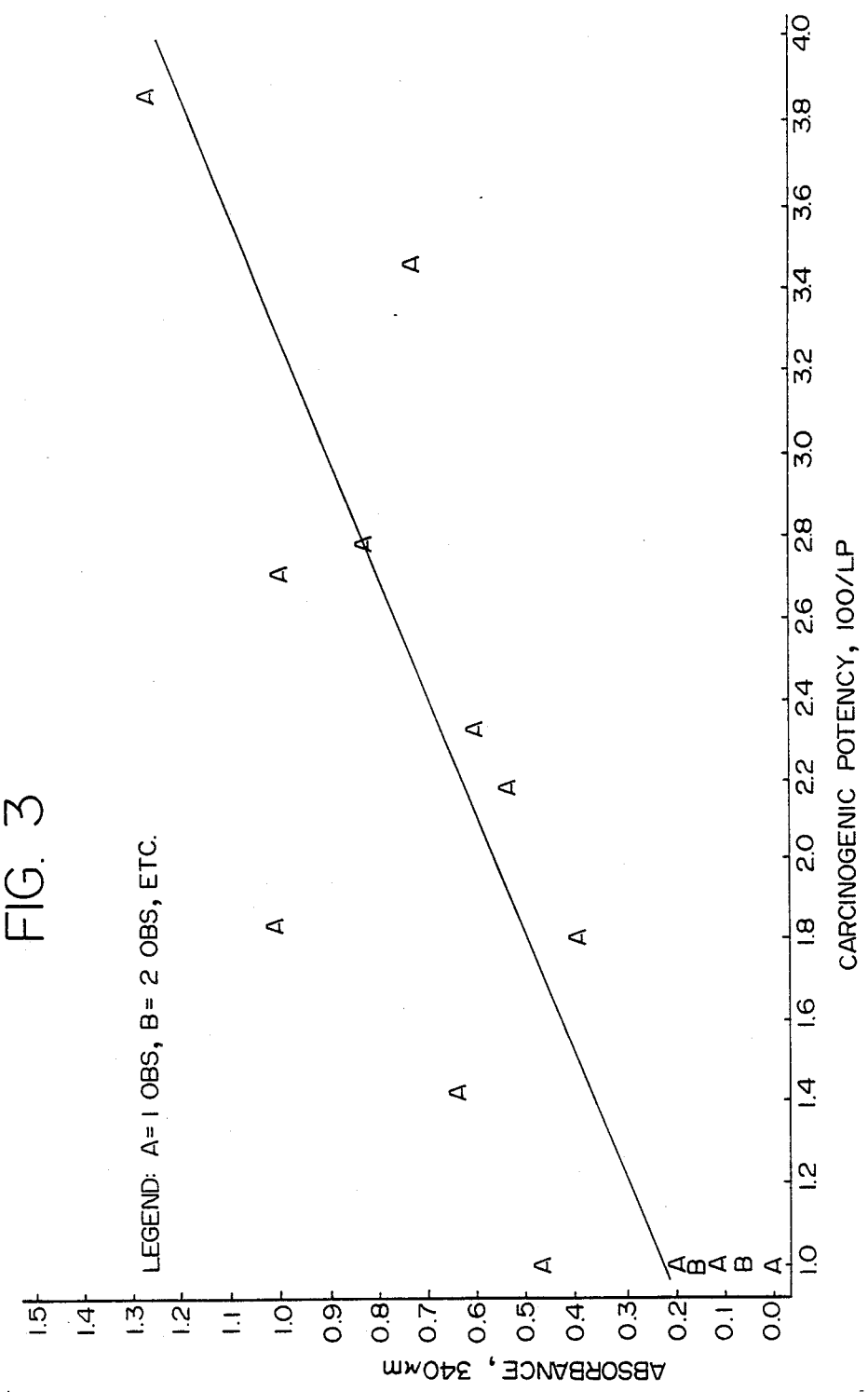

ASSAYING OF POLYNUCLEAR AROMATIC COMPOUNDS

FIELD OF THE INVENTION

This invention is concerned broadly with a method for the assaying of polynuclear aromatics (PNAs). It is more specifically concerned with a rapid chemical method for the assaying of the PNAs in a complex mixture of hydrocarbons. It is further concerned with evaluating the mutagenicity of hydrocarbon mixtures derived from petroleum.

BACKGROUND OF THE INVENTION

It is generally known that petroleum consist of a complex mixture of many hydrocarbons, including the so-called polynuclear aromatics (PNAs). These PNAs, being relatively high boiling, are substantially absent in distillation cuts boiling below 500° F., but are found in higher boiling fractions in increasing concentration as the boiling point increases, and in the residuum. Materials classed as PNAs have from three to seven or more condensed rings, some of which may be partially saturated, and they usually have one or more alkyl and/or cycloalkyl side chains of various molecular weights. In addition, some of the PNAs contain sulfur as a heteroatom, and may only be separated from the pure hydrocarbon PNAs with great difficulty, if at all. It is also known that the content of PNAs, and probably the distribution of their molecular weights, vary with the petroleum source. See "Encyclopedia of Chemical Technology", Kirk-Othmer, 3rd Edition, *Petroleum Composition*, Vol. 17, pp 119–129, incorporated herein by reference as background material.

PNAs are of importance for at least two reasons. In petroleum refining, they may adversely affect the practical properties of certain lubricants and other products. In such instances, they usually are removed or converted to other hydrocarbons types. And, ecologically, some of the PNAs are recognized to have dermal carcinogenic activity.

The generally accepted method for evaluating the carcinogenic activity of petroleum products involves animal tests in which animals such as mice are exposed to the hydrocarbon by painting a portion of the skin repeatedly over a long period of time, and evaluating the tendency of such exposure to produce malignant growths. It is generally recognized that this test method requires seventy to eighty weeks of exposure to produce reliable results, and therefore that the method is not suited for situations in which a quick indication of potential carcinogenic activity is required.

In vitro mutagenic activity assays, such as, for example, the *Salmonella* Microsomal Activation Assay described by B. N. Ames, J. McCann, and E. Yamasaki in *Mutat. Research*, 31, 347–364 (1975), hereinafter referred to as the "Ames test", provide a rapid, inexpensive method for screening chemicals for carcinogenic potential. The entire content of this publication is incorporated herein by reference as if fully set forth. In general, the predictability of this assay with simple chemicals is good; validation studies have produced a 65–90% correlation between mutagenic activity and carcinogenic activity for many relatively pure compounds. However, the assay is unsuited to the testing of water insoluble complex mixtures, such as the complex hydrocarbon mixtures encountered in petroleum refinery streams. Attempts to use the Ames test procedure with such materials give results which are not reproducible and do not relate in a significant way to the known carcinogenic activity for previously tested mixtures.

Blackburn et al. U.S. Pat. No. 4,499,187 discloses a modification of the Ames test, hereinafter referred to as the "Modified Ames Test" suitable for use with complex hydrocarbon mixtures. The modification, in essence, involves the preparation of a DMSO (dimethylsulfoxide) extract of the sample being evaluated, and use of the DMSO extract instead of the sample itself in the Ames test together with an optimal amount of metabolic activator such as induced rat liver homogenate S-9. Detailed descriptions of the method for preparing the extract and for the assay itself are given in U.S. Pat. No. 4,499,187, the entire content of which is incorporated herein by reference. The Modified Ames Test, unlike the Ames test itself, provides a rapid and reproducible measure of the mutagenic activity of petroleum hydrocarbon mixtures, and the results of such assays strongly correlate with the carcinogenic activity index found for the mixtures by skin painting.

The Modified Ames Test described above is much more rapid than skin painting, requiring only about two to three days to complete an assay compared with 18 months. There remains a need, however, for a less labor-intensive and less costly assay.

It is an object of this invention to provide a rapid, inexpensive and very sensitive chemical method for assaying the PNA content of a hydrocarbon oil. It is a further object to provide a rapid chemical method for assaying the mutagenicity and potential carcinogenic potency of a hydrocarbon oil derived from petroleum. It is a still further object of this invention to provide a rapid method for controlling certain petroleum refinery processes wherein PNAs are segregated, such as solvent extraction. These and other objects will become evident to one skilled in the art on reading this entire specification, including the appended claims.

BRIEF DESCRIPTION OF THE INVENTION

It has now been found that the PNA content of a complex hydrocarbon mixture is advantageously assayed by nitrating a sample of the mixture under relatively mild conditions followed by determining the absorbance of light by the nitrated PNAs, preferably at a suitable wavelength such as 340 nm (nanometers). As will be shown hereinbelow, the absorbance of the nitrated material is proportional to the PNA content of the original oil. It has further been found that for hydrocarbon oils derived from petroleum and that boil within the range of about 500° F. to 1000° F., there is a very strong correlation between the absorbance of the nitrated material and both the mutagenic activity of the original oil as determined by the Modified Ames Test and the Carcinogenic Potency determined by skin painting. Thus, the method of this invention provides a very fast and reproducible assay of the mutagenic activity of the oil.

The term "derived from petroleum" as used herein is intended to include petroleum fractions obtained by physical methods such as distillation, solvent extraction, and the like as well as such fractions that have been subjected to petroleum processes such as clay treating, hydrocracking, hydrofinishing, and the like.

BRIEF DESCRIPTION OF THE DRAWING

FIG. 1. Correlation of Absorbance at 340 nm with gravimetrically determined PNAs.

FIG. 2. Correlation of Absorbance at 340 nm with mutagenicity by Modified Ames Test.

FIG. 3. Correlation of Absorbance at 340 nm with Carcinogenic Potency from skin painting.

PREFERRED EMBODIMENTS AND BEST MODE

The preferred embodiments of the method of this invention including the best mode known to us will now be described.

A sample of the oil to be assayed is nitrated by the following procedure. To a known weight or volume of oil in about the 10 milligram range, and contained in 0.1 ml of cyclohexane, is added 1 ml of 80% nitric acid of reagent grade or better. This mixture is incubated at 80° C. for two hours. It is then neutralized by adding 1 ml of 10 Molar sodium hydroxide. The neutralized mixture is cooled and 5 ml of dichloromethane is added, mixed, and allowed to stand for phase separation. The upper, aqueous phase is then carefully withdrawn and discarded, particular attention being given to avoid losses of any of the dichloromethane phase. 100 microliters of the dichloromethane extract is withdrawn and added to 0.9 ml of DMSO. The absorbance of the DMSO solution, referred to hereinbelow as the "test sample", is then determined with a spectrophotometer at 340 nm.

Although it is contemplated that the method of this invention may be used to reliably determine the mutagenicity of a complex mixture of hydrocarbons from any source, it is particularly useful for rapidly estimating the potential dermal carcinogenicity of a complex hydrocarbon mixture derived from petroleum. As will be shown below, there is a very strong correlation between the absorbance at 340 nm derived by the method of this invention and carcinogenic potency for petroleum derived mixtures. The method of this invention is particularly useful for petroleum derived mixtures boiling within the range of about 500° F. to about 1000° F. For those oils that have a significant component boiling below 500° F. and/or above 1000° F., the correlation has been observed to deteriorate. With such mixtures, it is preferred to isolate the fraction boiling from about 500° F. to about 1000° F. prior to nitration. All references made herein to boiling point are to be understood to refer to the boiling point as determined by ASTM Method D-1160 (Distillation of Petroleum Products at Reduced Temperatures), published by the American Society for Testing Materials, 1916 Race Street, Philadelphia, Pa.

The term "absorbance" is used herein in the conventional sense and refers to log $(I_o/I)$ wherein $I_o$ and $I$ are the intensities of the incident light and the transmitted light, resp. All measurements reported herein are based on the same cell thickness.

Although DMSO is the presently preferred solvent for the nitrated material, it is contemplated that other solvents effective in solubilizing the nitrated oil also may be used.

This invention will now be illustrated by examples. The examples, however, are not to be construed as limiting the scope of the invention, which scope is determined by this entire specification including the appended claims.

EXAMPLES

Example 1

A data base was established using a series of twenty-one different petroleum oils and by-product extracts. These all boiled above about 500° F., and all but Sample No. 5 boiled within the range of about 500° F. to 1000° F. Sample No. 5, the hydrotreated bright stock extract contains components which boiled above 1000° F. Table I provides a description for each of the twenty-one oils.

Each of the oil samples was evaluated for mutagenicity by the Modified Ames Test using the slope of the linear portion of the dose-response curve, as described above, and by the method of this invention (reported as absorbance at 340 nm). Table II summarizes the results of the Mutagenicity Tests. and also the results of skin painting tests in terms of the observed LP (latent period) i.e. the average number of weeks elapsed before the development of a tumor, the number of animals that developed tumors, and the Carcinogenic Potency calculated as 100/LP. Oils that produced no tumors in 100 weeks are arbitrarily assigned a Carcinogenic Potency=1.00.

Table II also shows the gravimetrically determined total PNA concentration as wt. % of each oil. These values were obtained gravimetrically from the DMSO extracts of the oils, using a method similar to the one described for this purpose by the Institute of Petroleum, London (IP 24780).

It is here noted that not every one of the 21 samples described in Table I were included in Examples 2–4 which follow.

TABLE I

| Sample No. | Description |
|---|---|
| 1 | Hydrotreated Machine Oil Extract |
| 2 | Hydrotreated Machine Oil Extract |
| 3 | Hydrotreated Machine Oil Extract |
| 4 | Hydrotreated Machine Oil Extract |
| 5 | Hydrotreated Bright Stock Extract |
| 6 | Furfural Extracted Naphthenic Distillate |
| 7 | Technical White Oil ($SO_2$ Extracted/Hydrofinished) |
| 8 | Furfural Extracted/Ferrofined Paraffinic Distillate |
| 9 | Mildly Furfural Extracted/Polished Paraffinic Distillate |
| 10 | Light Medicinal Oil BP |
| 11 | Furfural Extracted/Polished Paraffinic Distillate |
| 12 | Distillate Aromatic Extract |
| 13 | $SO_2$/Benzene Extracted, Ferrofined Paraffinic Distillate |
| 14 | Acid/Earth Treated Naphthenic Distillate |
| 15 | $SO_2$ Extracted Napthenic Distillate |
| 16 | $SO_2$ Extracted, Earth Finished Naphthenic Distillate |
| 17 | Mildly Hydrotreated Naphthenic Distillate |
| 18 | Hydrotreated Neutralized Naphthenic Distillate |
| 19 | Hydrotreated Naphthenic Distillate |
| 20 | Low Viscosity Index Paraffinic Oil - Hydrotreated |
| 21 | Low Viscosity Index Paraffinic Oil - Hydrotreated |

TABLE II

| SAMPLE NO. | MUTAGEN. INDEX MODIFIED AMES | ABSORB- ANCE, 340 nm | LATENT PERIOD (LP) (WEEKS) | NUMBER ANIMALS WITH TUMOR(S) | CARCINO- GENIC POTENCY, 100/LP | WT % PNA's (GRAVI- METRIC) |
|---|---|---|---|---|---|---|
| 1 | 9.7 | 1.02 | 37 | 22 | 2.70 | 9.3 |
| 2 | 11.0 | .831 | 36 | 23 | 2.78 | 9.0 |
| 3 | 5.2 | 1.02 | 55 | 7 | 1.82 | 4.0 |
| 4 | 4.6 | .649 | 70 | 6 | 1.43 | 5.0 |
| 5[1] | 0.0 | .475 | — | 0 | 1.00 | 4.5 |
| 6 | 0.0 | .216 | — | 0 | 1.00 | 0.7 |
| 7 | 0.0 | .058 | — | 0 | 1.00 | 0.5 |
| 8 | 0.9 | .198 | 48 | 1 | 2.08 | 0.9 |
| 9 | 0.0 | .165 | — | 0 | 1.00 | 0.6 |
| 10 | 0.0 | .007 | — | 0 | 1.00 | 0.3 |
| 11 | 0.0 | .139 | — | 0 | 1.00 | 0.7 |
| 12 | 17.0 | 1.26 | 26 | 41 | 3.85 | 19.0 |
| 13[2] | 2.4 | .340 | 44 | 2 | 2.27 | 3.2 |
| 14[2] | 9.1 | .644 | 20 | 6 | 5.00 | 11.0 |
| 15 | 0.0 | .176 | 58 | 1 | 1.72 | 0.7 |
| 16 | 0.0 | .072 | — | 0 | 1.00 | 0.4 |
| 17[2] | 3.9 | .485 | 46 | 1 | 2.17 | 4.6 |
| 18 | 4.0 | .393 | 56 | 4 | 1.79 | 4.0 |
| 19 | 3.6 | .535 | 46 | 5 | 2.17 | 5.4 |
| 20 | 6.5 | .589 | 43 | 5 | 2.33 | 5.8 |
| 21 | 9.2 | .728 | 29 | 20 | 3.45 | 8.5 |

[1] This sample was not included in Examples 3 and 4; it contained material boiling above 1000° F.
[2] These samples were not included in Example 4 because the carcinogenic potency for these three oils was determined at a different dosage level than for the other 18 oils, and therefore is not comparable with the others.

Example 2

In this example the correlation of the absorbance at 340 nm and the gravimetrically determined total PNAs is shown in FIG. 1. The calculated sample correlation coefficient for the relationship is 0.87. In this and subsequent examples, the least squares regression line and the sample correlation coefficient are computed by the conventional procedures as given, e.g., in *Statistics Manual*, Edwin L. Crow et al., pp 152-159, Dover Publications, New York, N.Y. (1956), incorporated herein by reference.

Example 3

The correlation of the absorbance at 340 nm obtained by the method of this invention and shown in Table II with the Mutagenicity Index obtained by the Modified Ames Test is shown in FIG. 2. The calculated sample correlation coefficient is 0.93.

Example 4

The correlation of the absorbance at 340 nm obtained by the method of this invention and the Carcinogenic Potency by skin painting are shown in FIG. 3. The calculated sample correlation coefficient is 0.84.

It is evident from the foregoing examples that the method of this invention provides a sensitive assay of total PNAs, as well as a test for mutagenicity which is rapid, simpler, and much less costly than the Ames Test, and yet it provides highly significant prediction of carcinogenic potency. While not wishing to be bound by theory, it is believed that the observed correlations result from the mutagenic polynuclear aromatics contained in the oils evaluated.

Although the method of this invention has been exemplified with hydrocarbon mixtures derived from petroleum, it is contemplated that the method may be used with hydrocarbon mixtures derived from other fossil fuels such as coal and tar sands.

Because determinations of PNA content by the method of this invention are very sensitive and very rapid, requiring about 20 minutes for an assay, the method lends itself not only to the determination of mutagenicity as described above, but also to other applications for which a determination of the PNA content may be relevant. For example, in the solvent extraction process as applied to heavy oils to selectively remove aromatics, the quality of the product and the efficiency of the process may be advantageously monitored by the method provided herein. It is also contemplated to monitor environmental samples for relative PNA content and potential mutagenicity by use of the method of this invention.

U.S. patent application Ser. No. 07/018,119 filed on even date herewith provides a biochemical method for evaluating the mutagenic activity of hydrocarbon mixtures.

What is claimed is:

1. A method for evaluating the mutagenic activity of a petroleum oil substantially free of material boiling below 500° F. and of material boiling above 1000° F., which method comprises:
   contacting a sample of said petroleum oil with nitric acid under conditions effective to nitrate the aromatic components thereof;
   recovering from said nitric acid contacted petroleum oil a mixture including any nitrated aromatics present;
   determining the light absorbance of said recovered mixture; and
   determining the mutagenicity index from a standard curve relating absorbance of nitrated oils at 340 nm with the corresponding mutagenicity index of unnitrated oils determined by the modified Ames Test, said standard curve being obtained from a random set of samples of varying mutagenicity.

2. The method of claim 1 wherein said determination of light absorbance is made with a spectrophotometer at 340 nm.